(12) United States Patent
Blanchard et al.

(10) Patent No.: US 8,668,739 B2
(45) Date of Patent: Mar. 11, 2014

(54) UNITARY ORTHOPEDIC IMPLANT

(75) Inventors: Cheryl Blanchard, Fort Wayne, IN (US); Erin Johnson, Columbia City, IN (US); Michael Hawkins, Columbia City, IN (US); Hallie Brinkerhuff, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 151 days.

(21) Appl. No.: 13/204,083

(22) Filed: Aug. 5, 2011

(65) Prior Publication Data
US 2012/0046752 A1 Feb. 23, 2012

Related U.S. Application Data

(60) Provisional application No. 61/375,594, filed on Aug. 20, 2010.

(51) Int. Cl.
*A61F 2/38* (2006.01)
(52) U.S. Cl.
USPC ..................................... 623/14.12; 623/18.11
(58) Field of Classification Search
USPC ................................. 623/14.12, 16.11, 18.11
See application file for complete search history.

(56) References Cited

U.S. PATENT DOCUMENTS

| | | | |
|---|---|---|---|
| 4,502,161 A | 3/1985 | Wall | |
| 4,839,215 A | 6/1989 | Starling et al. | |
| 4,966,924 A | 10/1990 | Hyon et al. | |
| 5,041,138 A | 8/1991 | Vacanti et al. | |
| 5,067,964 A | 11/1991 | Richmond et al. | |
| 5,147,904 A | 9/1992 | Jochum et al. | |
| 5,282,861 A | 2/1994 | Kaplan | |
| 5,314,478 A | 5/1994 | Oka et al. | |
| 5,358,525 A | 10/1994 | Fox et al. | |
| 5,458,643 A | 10/1995 | Oka et al. | |
| 5,556,429 A | 9/1996 | Felt | |
| 5,607,474 A | 3/1997 | Athanasiou et al. | |
| 5,645,592 A | 7/1997 | Nicolais et al. | |

(Continued)

FOREIGN PATENT DOCUMENTS

| DE | 2933174 | 4/1980 |
|---|---|---|
| DE | 19721661 | 11/1998 |

(Continued)

OTHER PUBLICATIONS

Quinton, J.S., et al., "Characterizing the Bonding Mechanisms at Silane-Metal interfaces: A Model System", Journal of Material Science Letters, vol. 18, pp. 1833-1835, dated Nov. 1999.

(Continued)

*Primary Examiner* — Thomas J Sweet
*Assistant Examiner* — Megan Wolf
(74) *Attorney, Agent, or Firm* — Schwegman, Lundberg & Woessner, P.A.

(57) ABSTRACT

The present disclosure relates to an orthopedic implant that may be used to repair and/or replace focal defects in an individual's articular cartilage. In one exemplary embodiment, the present invention provides a unitary orthopedic implant that includes a bone contacting layer and an articulating layer. In exemplary embodiments, the bone contacting layer may have a thickness of between about 1 millimeter and 3 millimeters. In exemplary embodiments, the articulating layer may have a thickness of between about 1 millimeter and 2 millimeters. As a result, the orthopedic implant may have an overall thickness of between about 2 millimeters and about 5 millimeters.

20 Claims, 7 Drawing Sheets

(56) References Cited

U.S. PATENT DOCUMENTS

| | | | |
|---|---|---|---|
| 5,658,343 A | 8/1997 | Hauselmann et al. | |
| 5,702,397 A | 12/1997 | Goble et al. | |
| 5,795,353 A | 8/1998 | Felt | |
| 6,120,541 A * | 9/2000 | Johnson | 623/14.12 |
| 6,132,468 A | 10/2000 | Mansmann | |
| 6,140,452 A | 10/2000 | Felt et al. | |
| 6,179,840 B1 | 1/2001 | Bowman | |
| 6,224,630 B1 | 5/2001 | Bao et al. | |
| 6,231,605 B1 | 5/2001 | Ku | |
| 6,306,177 B1 | 10/2001 | Felt et al. | |
| 6,425,923 B1 | 7/2002 | Stalcup et al. | |
| 6,443,988 B2 | 9/2002 | Felt et al. | |
| 6,447,514 B1 | 9/2002 | Stalcup et al. | |
| 6,494,917 B1 | 12/2002 | McKellop et al. | |
| 6,530,956 B1 | 3/2003 | Mansmann | |
| 6,533,818 B1 | 3/2003 | Weber et al. | |
| 6,547,828 B2 | 4/2003 | Scott et al. | |
| 6,620,196 B1 | 9/2003 | Trieu | |
| 6,629,997 B2 | 10/2003 | Mansmann | |
| 6,679,913 B2 | 1/2004 | Homsy | |
| 6,719,797 B1 | 4/2004 | Ferree | |
| 6,733,533 B1 | 5/2004 | Lozier | |
| 6,827,743 B2 | 12/2004 | Eisermann et al. | |
| 6,994,730 B2 | 2/2006 | Posner | |
| 7,001,431 B2 | 2/2006 | Bao et al. | |
| 7,077,865 B2 | 7/2006 | Bao et al. | |
| 7,559,932 B2 | 7/2009 | Truckai et al. | |
| 7,670,381 B2 * | 3/2010 | Schwartz | 623/17.17 |
| 7,857,817 B2 | 12/2010 | Tallarida et al. | |
| 7,901,457 B2 | 3/2011 | Truncale et al. | |
| 2001/0033857 A1 | 10/2001 | Vyakarnam et al. | |
| 2001/0039455 A1 | 11/2001 | Simon et al. | |
| 2002/0022884 A1 | 2/2002 | Mansmann | |
| 2002/0029083 A1 | 3/2002 | Zucherman et al. | |
| 2002/0156531 A1 | 10/2002 | Felt et al. | |
| 2002/0173855 A1 | 11/2002 | Mansmann | |
| 2002/0183845 A1 | 12/2002 | Mansmann | |
| 2002/0193883 A1 | 12/2002 | Wironen | |
| 2003/0008396 A1 | 1/2003 | Ku | |
| 2003/0074076 A1 | 4/2003 | Ferree et al. | |
| 2003/0078617 A1 | 4/2003 | Schwartz et al. | |
| 2003/0195628 A1 | 10/2003 | Bao et al. | |
| 2003/0220649 A1 | 11/2003 | Bao et al. | |
| 2004/0010312 A1 | 1/2004 | Enayati | |
| 2004/0039447 A1 | 2/2004 | Simon et al. | |
| 2004/0051213 A1 | 3/2004 | Muratoglu | |
| 2004/0133275 A1 | 7/2004 | Mansmann | |
| 2004/0138754 A1 | 7/2004 | Lang et al. | |
| 2004/0153163 A1 | 8/2004 | Posner | |
| 2004/0163681 A1 | 8/2004 | Verhaverbeke | |
| 2004/0199250 A1 | 10/2004 | Fell | |
| 2004/0236424 A1 | 11/2004 | Berez et al. | |
| 2005/0043808 A1 | 2/2005 | Felt et al. | |
| 2005/0125077 A1 | 6/2005 | Harmon et al. | |
| 2005/0171604 A1 | 8/2005 | Michalow | |
| 2005/0251149 A1 | 11/2005 | Wenz | |
| 2005/0251266 A1 | 11/2005 | Maspero et al. | |
| 2005/0287187 A1 | 12/2005 | Mansmann | |
| 2006/0009853 A1 | 1/2006 | Justin et al. | |
| 2006/0079905 A1 | 4/2006 | Beyar et al. | |
| 2006/0224244 A1 | 10/2006 | Thomas et al. | |
| 2006/0235542 A1 | 10/2006 | Hodorek et al. | |
| 2006/0253200 A1 | 11/2006 | Bao et al. | |
| 2007/0027230 A1 | 2/2007 | Beyar et al. | |
| 2007/0038300 A1 | 2/2007 | Bao et al. | |
| 2007/0088444 A1 | 4/2007 | Hodorek et al. | |
| 2007/0142916 A1 | 6/2007 | Olson, Jr. et al. | |
| 2007/0250164 A1 * | 10/2007 | Troxel | 623/14.12 |
| 2007/0276506 A1 | 11/2007 | Troxel | |
| 2008/0195205 A1 | 8/2008 | Schwartz | |

FOREIGN PATENT DOCUMENTS

| | | |
|---|---|---|
| DE | 20303205 U | 4/2003 |
| DE | 10220368 | 12/2003 |
| EP | 0528080 A1 | 2/1993 |
| WO | WO 2005/038016 A1 | 4/2005 |
| WO | WO 2005/051242 A1 | 6/2005 |
| WO | WO 2006/060555 A1 | 6/2006 |
| WO | WO 2009/115616 A1 | 9/2009 |
| WO | WO 2010/014446 A1 | 2/2010 |
| WO | WO-2012023032 A1 | 2/2012 |

OTHER PUBLICATIONS

PCT International Search Report and Written Opinion for PCT/US2007/061270 dated Feb. 6, 2008.

Notification of Transmittal of PCT International Search Report and Written Opinion for PCT/IB2011/001908 dated Dec. 19, 2011.

International Application Serial No. PCT/IB2011/001908, International Preliminary Report on Patentability mailed Aug. 8, 2012, 7 pgs.

International Application Serial No. PCT/IB2011/001908, International Search Report mailed Dec. 19, 2011, 4 pgs.

* cited by examiner

UNITARY ORTHOPEDIC IMPLANT

The present application claims the benefit of U.S. provisional patent application Ser. No. 61/375,594, filed Aug. 20, 2010, which is hereby incorporated by reference.

BACKGROUND

1. Field of the Disclosure

The present disclosure relates to an orthopedic implant. More particularly, the present disclosure relates to an orthopedic implant that may be used to repair and/or replace focal defects in an individual's articular cartilage.

2. Description of the Related Art

Due to a variety of factors, an individual may develop defects in the articular cartilage of a bone. For example, an individual may develop a focal defect in the articular cartilage of the femur and/or tibia in the knee joint. FIG. 1 depicts an illustration of a femur tibia joint 1 which includes a femur 2 and tibia 3. Condyle 4 of femur 2 has a tissue defect 5. More particularly, defect 5 is a defect of the articular cartilage. In some instances, defect 5 may extend through the articular cartilage and into the bone of femur 2.

Such defects may be rather small in size, but can cause the individual to experience substantial pain during joint articulation. Additionally, these defects may develop on opposing sides of the joint (i.e., in the articular cartilage of both femur 2 and tibia 3) and, during articulation of the joint, the defects may come into contact with one another, i.e., may form "kissing legions". In situations where the walls of opposing kissing legions come in contact, they may frictionally engage one other in a manner that exerts sufficient forces on the legions to cause further damage to the articular cartilage and, correspondingly, cause the legions to increase in size. As a result, with successive articulation of the joint, the legions may continue to expand and extend into the bone.

Current treatment options for repairing focal defects, such as kissing legions, can be effective. For example, mosaicplasty may be performed, which uses a bone plug to replace the cartilage in the area of the focal defect. FIG. 2 shows a cross-sectional view of a femur tibial joint in which bone plugs 6 have been implanted into femur 4. Femur 2 has inner cancellous bone 7 and covered by outer dense contact bone 8. The compact bone of the femur in the condyle region is covered by a layer of articular cartilage 9. Tibia 3 includes similar bone and cartilage structure. In order to insert bone plugs 6, a hole for the receipt of bone plug 6 must be formed through the articular cartilage layer 9 and into the individual's compact bone 8 and cancellous bone 7, resulting in a loss of some of the individual's natural bone stock. Additionally, if the bone plug 6 is taken from the individual, i.e., is an autograft, an additional incision may need to be made and the patient will also experience increased healing time and additional pain. Bone plugs 6 typically include the same tissue and structure of the area being repaired. That is, bone plugs 6 include a cancellous bone portion 11, a compact bone portion 13 and an articular cartilage portion 15. Alternatively, if the bone plug 6 is taken from another individual, i.e., is an allograft, the supply of bone may be extremely small, which may effectively prevent individuals from receiving the necessary mosaicplasty. Bone plugs 6 are inserted through each of the cartilage layer 9 and compact bone layer 8 and into the cancellous bone 7.

Additionally, the bone plugs used in conjunction with mosaicplasty generally have very small articulating surfaces and, as a result, the number of bone plugs necessary to effectively repair and/or replace a focal defect may be substantial. These deficiencies are compounded when the legions cooperate to form kissing legions that require the performance of mosaicplasty techniques on both sides of the articulating joint.

SUMMARY

The present disclosure relates to an orthopedic implant that may be used to repair and/or replace focal defects in an individual's articular cartilage. In one exemplary embodiment, the present invention provides a unitary orthopedic implant that includes a bone contacting layer and an articulating layer. In exemplary embodiments, the bone contacting layer may have a thickness of between about 1 millimeter and about 3 millimeters. In exemplary embodiments, the articulating layer may have a thickness of between about 1 millimeter and about 2 millimeters. As a result, the orthopedic implant may have an overall thickness of between about 2 millimeters and about 5 millimeters.

In exemplary embodiments of the present orthopedic implant, the bone contacting layer may be formed from a first material and the articulating layer may be formed from a second material that is different than the first material. In exemplary embodiments, the bone contacting layer may be formed from a material that facilitates bone ingrowth, such as a porous metal. In one exemplary embodiment, the bone contacting layer is formed from a material manufactured using Trabecular Metal™ technology, as described in detail below. In exemplary embodiments, the articulating layer may be formed from a polymer, a metal, or a combination thereof. The articulating layer may be secured to the bone contacting layer in any known manner, such as by interdigitation of a polymer articulating layer into the porous of a porous metal bone contacting layer.

In another exemplary embodiment, the orthopedic implant of the present invention may be secured to the individual's natural bone stock using a bone anchor. For example, the orthopedic implant may be positioned on the individual's bone in the location of the legion, such that the orthopedic implant covers the legion. Additionally, the periphery of the implant may be positioned beneath healthy cartilage. Then, a bone anchor may be positioned through the orthopedic implant in order to secure the orthopedic implant to the bone. In one exemplary embodiment, the bone anchor includes a head and a shaft. The shaft of the bone anchor may be threaded and the threaded shaft of the bone anchor may be threaded into the bone until the head of the bone anchor is secured against the articulating layer of the implant. In this manner, the head of the bone anchor functions to secure the implant in position as described in detail below. In one exemplary embodiment, the bone anchor may be formed from a bioresorbable material.

Advantageously, by forming the bone contacting layer from a material that facilitates bone ingrowth and/or attachment to the underlying bone, the need to remove a portion of the individual's bone for receipt of a bone plug is eliminated. Additionally, due to the decreased overall thickness of the orthopedic implant of the present invention relative to known bone plugs and cartilage replacement devices, the orthopedic implant may have a thickness that is substantially similar to the natural cartilage adjacent to the implant site. Further, the orthopedic implant may be formed to cover a substantially greater area than known bone plugs. This allows a single orthopedic implant to be used instead of a plurality of bone plugs as may be required by known mosaicplasty techniques. Additionally, when a bioresorbable bone anchor is used to secure the orthopedic implant of the present invention in position, the bone anchor will be adsorbed by the individual's body as the bone contacting layer begins to provide osseointegration, which eliminates both the need for a permanent bone anchor and the need to remove the bone anchor once osseointegration is established.

In one form thereof, the present invention provides an orthopedic implant including a first layer formed from a first material, the first layer having a thickness of less than 3 millimeters; and a second layer fixedly secured to the first layer, the second layer formed from a second material, the second layer having a thickness of less than 2 millimeters, wherein the second material is different than the first material.

In another form thereof, the present invention provides an orthopedic implant for repairing an articular cartilage defect including a bone contacting layer formed from a first material. The bone contacting layer also includes a top surface and a bottom bone contacting surface and has a thickness of less than about 3 millimeters between the top surface and bottom bone contacting surface. The implant also includes an articulating layer at least partially superimposed over the bone contacting layer. The articulating layer is formed from a second material that is different from the first material. The articulating layer also includes a top articulating surface and a bottom surface wherein the articulating layer has a thickness of less than about 2 millimeters between the top and bottom surfaces of the articulating layer.

In a further form thereof, the present invention provides an orthopedic implant for repairing an articular cartilage defect including a bone contacting layer formed from a first material and having an outer periphery. The bone contacting layer includes a top surface, a bottom bone contacting surface and one or more sidewalls extending therebetween. The bone contacting layer has a thickness of less than about 3 millimeters between the top surface and the bottom bone contacting surface. The implant also includes an articulating layer at least partially superimposed over the bone contacting layer and formed from a second material that is different from the first material. The articulating layer includes a top articulating surface and a bottom surface and has a thickness of less than about 2 millimeters between the top articulating surface and the bottom surface of the articulating layer. Additionally, the articulating layer has an outer periphery that is smaller than the outer periphery of the bone contacting layer.

In yet another form thereof, the present invention provides an orthopedic device for repairing an articular cartilage defect including an implant having an articulating layer at least partially superimposed over of bone contacting layer. The implant further includes a plurality of sections separated by slots wherein the sections fold relative to each other. The bone contacting layer is formed from a first material and includes a top surface and a bottom bone contacting surface. The bone contacting layer has a thickness of less than about 3 millimeters between the top surface and bottom bone contacting surface. The articulating layer is formed from a second material that is different from the first material. The articulating layer also includes a top articulating surface and a bottom surface, wherein the articulating layer has a thickness of less than about 2 millimeters between the top articulating surface and the bottom surface of the articulating layer.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner

DETAILED DESCRIPTION

Figure 3:
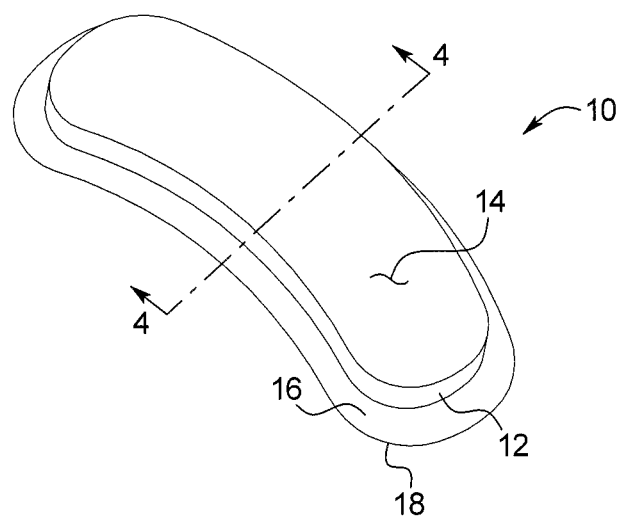
FIG. 3 is a perspective view of an exemplary embodiment of the orthopedic implant of the present invention having a bone contacting layer and an articulating layer.
Figure 4:
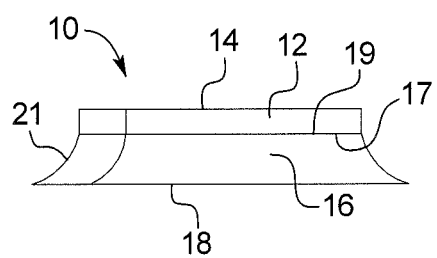
FIG. 4 is a cross-sectional view of the orthopedic implant of FIG. 3 taken along line 4-4 of FIG. 3.

Referring to FIGS. 3 and 4, orthopedic implant 10 is shown. Orthopedic implant 10 includes articulating layer 12, which defines a top or articulating surface 14 and a bottom surface 17 (FIG. 4). Orthopedic implant 10 also includes a bone contacting layer 16, which defines a bottom or bone contacting surface 18 and a top surface 19 (FIG. 4). Articulating layer 12 is at least partially superimposed over bone contacting layer 16. Orthopedic implant 10 is formed as a unitary implant, such that articulating layer 12 and bone contacting layer 16 are secured to one another.

As indicated above, in exemplary embodiments, bone contacting layer 16 may be formed from a first material and articulating layer 12 may be formed from a second material that is different than the first material. For example, bone contacting layer 16 may be formed from a material that facilitates bone ingrowth, such as a porous material. The porous material used to form bone contacting layer 16 may be any porous material, such as fiber metals, metal foams (such as Titanium foams, including cancellous structured titanium), ceramic foams (such as zirconia or alumnia foams), foams manufactured from metallic glasses, and/or a material manufactured using Trabecular Metal™ technology generally available from Zimmer, Inc., of Warsaw, Ind. "Trabecular Metal" is a trademark of Zimmer, Inc. A material manufactured using Trabecular Metal technology may be formed from a reticulated vitreous carbon (RVC) foam substrate which is infiltrated and coated with a biocompatible metal in the manner disclosed in detail in U.S. Pat. No. 5,282,861 to Kaplan, the disclosure of which is expressly incorporated herein by reference. The resulting, coated material is lightweight, strong, and has open cells that resemble the structure of natural cancellous bone, thereby providing a matrix into which cancellous bone may grow to fix the orthopedic implant to the patients bone.

Additionally, bone contacting layer 16 may have different porosities. For example, in one exemplary embodiment, bone contacting layer 16 has a thickness having a first, higher porosity adjacent to bone contacting surface 18 and a thickness having a second, lower porosity adjacent to articulating layer 12. Bone contacting layer 16 may also have a porosity gradient, such that the porosity of bone contacting layer 16 gradually changes over the thickness of bone contacting layer 16. In this embodiment, bone contacting layer may gradually decrease in porosity from bone contacting surface 18, where bone contacting layer 16 has its greatest porosity, until reaching top surface 19 adjacent to articulating layer 12, where bone contacting layer 16 has its lowest porosity. Alternatively, bone contacting layer 16 may have a greater porosity at top surface 19 adjacent to articulating layer 12. This may be advantageous when, for example, articulating layer 12 is secured to bone contacting layer 16 by interdigitation, as described below.

In exemplary embodiments, bone contacting layer 16 has a thickness between bottom bone contacting surface 18 and top surface 19 of between about 1 millimeter and about 3 millimeters. In one embodiment, the thickness is less than 3 millimeters. The thickness of bone contacting layer 16 may vary depending on the desired stiffness of the overall construct, e.g., the desired stiffness of orthopedic implant 10, or other desired properties. Additionally, the thickness of bone contacting layer 16 may be constant or vary throughout the layer.

Still referring to FIGS. 3 and 4 and turning to articulating layer 12, in exemplary embodiments, articulating layer 12 may be formed from a polymer, a metal, a hydrogel, or any combination thereof. For example, articulating layer 12 may be formed from polyetheretherketone (PEEK), polyethylenes, antioxidant stabilized polyethylene (such as Vitamin E stabilized polyethylene), polycarbonate urethane, polyacrylates (e.g. polymethacrylate, polyhydroxyethylmethacrylate (polyHEMA), and polyhydroxypropylmethacrylate), polyvinylpyrollidone (PVP), polyvinyl alcohol (PVA), polyacrylamides, polyacrylonitriles, polysaccharides (e.g. carrageenans and hyaluronic acid), polyalginates, polyethylene oxides (e.g. polyethylene glycol (PEG) and polyoxyethylene), polyamines (e.g. chitosan), polyurethanes (e.g. diethylene glycol and polyoxyalkylene diols), and other biomedical polymers. Additionally, articulating layer 12 may be formed from other biocompatible materials, such as cobalt chromium, stainless steel, titanium, and ceramics (such as zirconia and alumina).

As indicated above, in some embodiments, articulating layer 12 may be formed form a material that is different than the material forming bone contacting layer 16. For example, articulating layer 12 may be formed from a polymer, such as PEEK, while bone contacting layer 16 is formed from a porous material, such as a material manufactured using Trabecular Metal technology. Additionally, in embodiments that utilize two different orthopedic implants 10 that may articulate against one another, such as in the treatment of kissing legions, articulating layer 12 and surface 14 of each of orthopedic implants 10 may be formed from a different material. Advantageously, by forming articulating layers 12 from different materials, the frictional forces experienced by articulating layers 12 during joint articulation may be reduced. Additionally, implants 10 are not restricted to articulating against each other, but may articulate against natural articular cartilage. For example, implants 10 may easily transition back and forth between articulating against opposing implants 10 and natural articular cartilage during normal joint articulation.

In exemplary embodiments, articulating layer 12 may have a thickness between top articulating surface 14 and bottom surface 17 of between about 1 millimeter and about 2 millimeters. In one embodiment, the thickness may be less than about 2 millimeters. The thickness of articulating layer 12 may vary depending on the thickness of the cartilage adjacent to the implant site. Specifically, the thickness of articulating layer 12 may be adjusted to allow the thickness of implant 10 to correspond to the thickness of the individual's cartilage at or near the area of implantation of implant 10. Additionally, the thickness of articulating layer 12 may be constant or vary throughout the layer. Furthermore, the overall thickness of implant 10 may be between about 2 millimeters and about 5 millimeters.

As indicated above and as shown in FIGS. 3 and 4, orthopedic implant 10 is a unitary, monolithic implant. In order to form implant 10, articulating layer 12 and bone contacting layer 16 are joined to one another. Articulating layer 12 and bone contacting layer 16 may be joined to one another using any known method, such as the use of adhesives, mechanical interlocking, plasma spraying, injection molding, casting, polymerization, and/or welding (including ultrasonic, laser, and resistance welding). In one exemplary embodiment, articulating layer 12 is formed from a polymer, such as PEEK, that is compression molded into bone contacting layer 16, which may be formed from a material manufactured using Trabecular Metal technology and primed to receive the polymer. In this embodiment, the polymer forming articulating layer 12 is interdigitated into the pores of the material forming bone contacting layer 16 to create a mechanical interlock that secures articulating layer 12 to bone contacting layer 16.

In other exemplary embodiments, articulating layer 12 may be formed from a polymer that is functionalized and bone contacting layer 16 may be formed from a porous material, such as a material manufactured using Trabecular Metal Technology, that has been surface treated to facilitate the formation of a bond with articulating layer 12. Alternatively, bone contacting layer 16 may be formed from a woven material and/or a polyethylene that is applied directly to a substrate formed from a porous material. In this embodiment, the woven material and/or polyethylene forming a portion of bone contacting layer 16 may form tendrils that would provide for and facilitate the connection of articulating layer 12 to bone contacting layer 16. In other exemplary embodiments, bone contacting layer 16 may be made of a porous material, while articulating layer 12 may be made from a metal, such as titanium or a titanium alloy. In this embodiment, a thin film of titanium may be diffusion bonded to the porous material of bone contacting layer 16 to form articulating layer 12.

Figure 1:
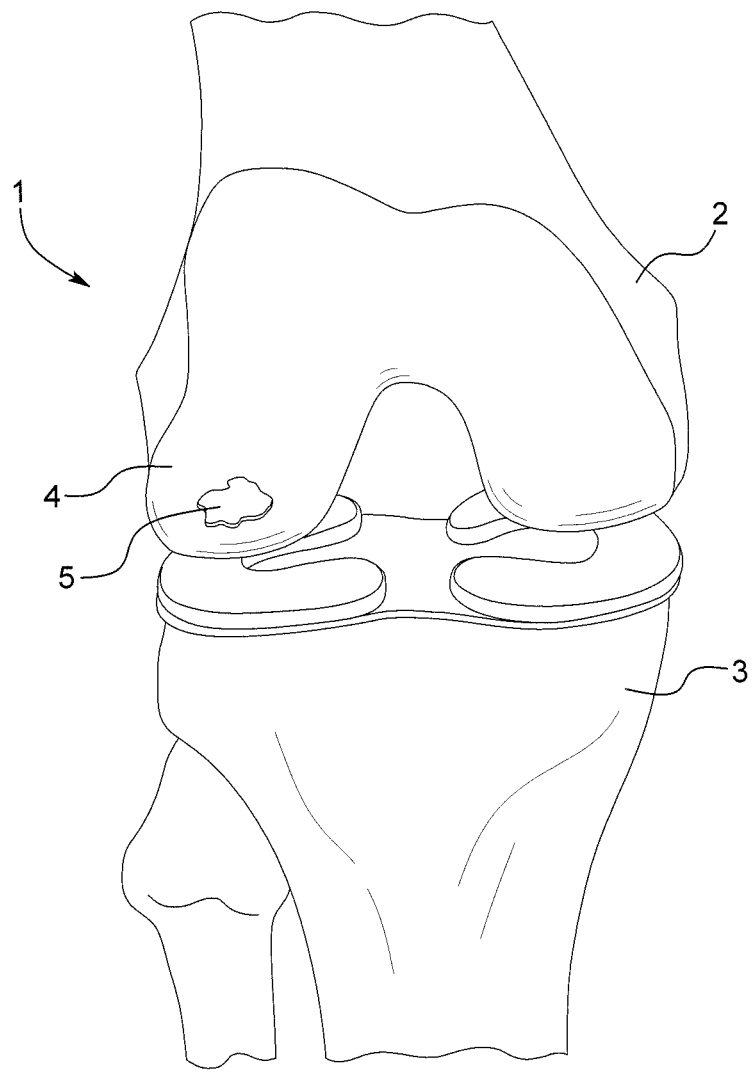
FIG. 1 is a perspective view of a knee joint including a femur having damage or diseased cartilage.

Implant 10 may be formed in any desired shape and size. For example, implant 10 may have a specific shape that corresponds to the particular anatomy at the site where implant 10 is to be implanted. In exemplary embodiments, implant 10 may be formed to correspond to the anatomy of the meniscus, femoral condyles, trochlear groove, ankle, glenoid, humerus, and/or the femoral head. Implant 10 may also be shaped to have a rounded and/or curved external periphery, as shown in FIG. 1. For example, implant 10 may, but does not necessarily, have the reniform shape shown in FIG. 1. Alternatively, implant 10 may have a geometric shape that includes sharp corners, such as a triangle, square, or rectangle. Further, implant 10 may be formed to be oversized, i.e., may be larger than the anticipated treatment area, and may be cut or otherwise trimmed by the surgeon to the desired size prior to or during surgery.

In another exemplary embodiment, implant 10 may include a thread (not shown) fowled in the periphery of implant 10. The addition of a thread to the periphery of implant 10 would allow for implant 10 to be threaded into the surrounding tissue during implantation. In one exemplary embodiment, the thread extending around the periphery of implant 10 is formed as a coarse, shallow thread. In exemplary embodiments, the thread may extend less than entirely around the periphery of implant 10. For example, the thread may extend around about three-quarters, about one-half, about one-third, or about one-quarter of the periphery of implant 10.

Regardless of the form implant 10 takes, articulating surface 14 may have an area substantially equal to or less than about 1,500 mm$^2$. In exemplary embodiments, articulating surface 14 may have an area as small as 5 mm$^2$, 8 mm$^2$, 10 mm$^2$, 15 mm$^2$, 20 mm$^2$, or 25 mm$^2$ and as large as 50 mm$^2$, 100 mm$^2$, 250 mm$^2$, 500 mm$^2$, 750 mm$^2$, or 1,000 mm$^2$. In other exemplary embodiments, articulating surface 14 may have an area as small as 10 mm$^2$, 12 mm$^2$, 15 mm$^2$, 20 mm$^2$, or 25 mm$^2$ and as large as 30 mm$^2$, 35 mm$^2$, 40 mm$^2$, 50 mm$^2$, or 60 mm$^2$.

Bone contacting layer 16 includes one or more sidewalls 21. In the embodiment shown in FIG. 4, sidewall 21 is an arcuate continuous sidewall. In other embodiments, bone contacting layer 16 may include a plurality of straight sidewalls which intersect a various angles. Sidewall 21 may, but is not necessarily, tapered or angled from bottom bone contacting surface 18 to top surface 19. In other embodiments, sidewall 21 is straight between bottom bone contacting surface 18 and top surface 19 and does not include a taper.

Figure 2:
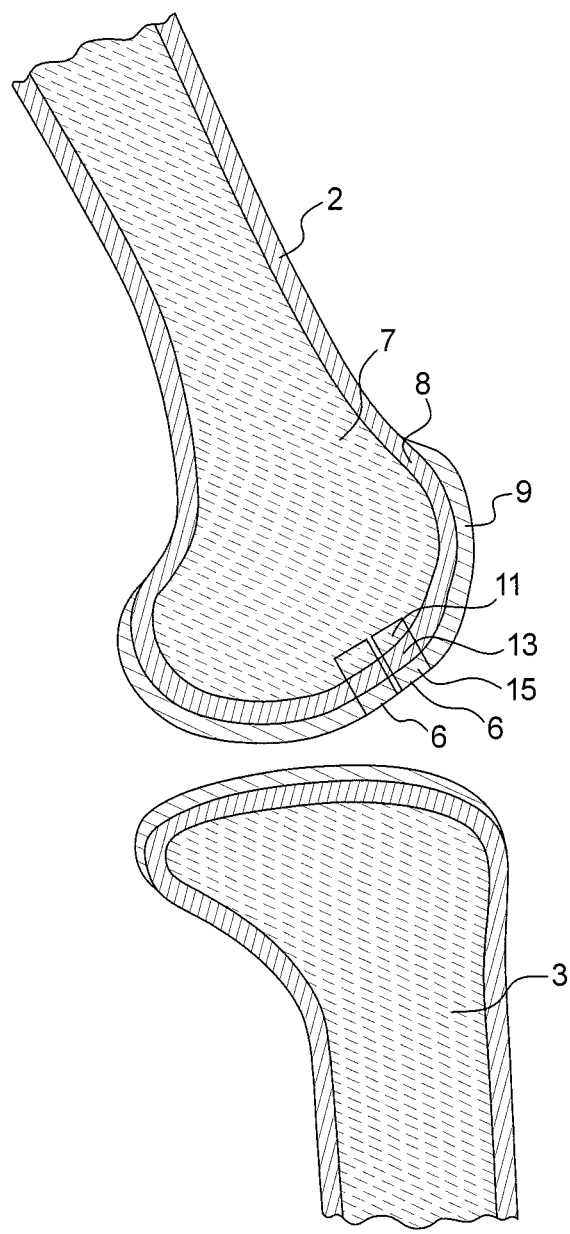
FIG. 2 is a cross-sectional view of a knee joint including prior art bone plugs implanted therein.
Figure 5:
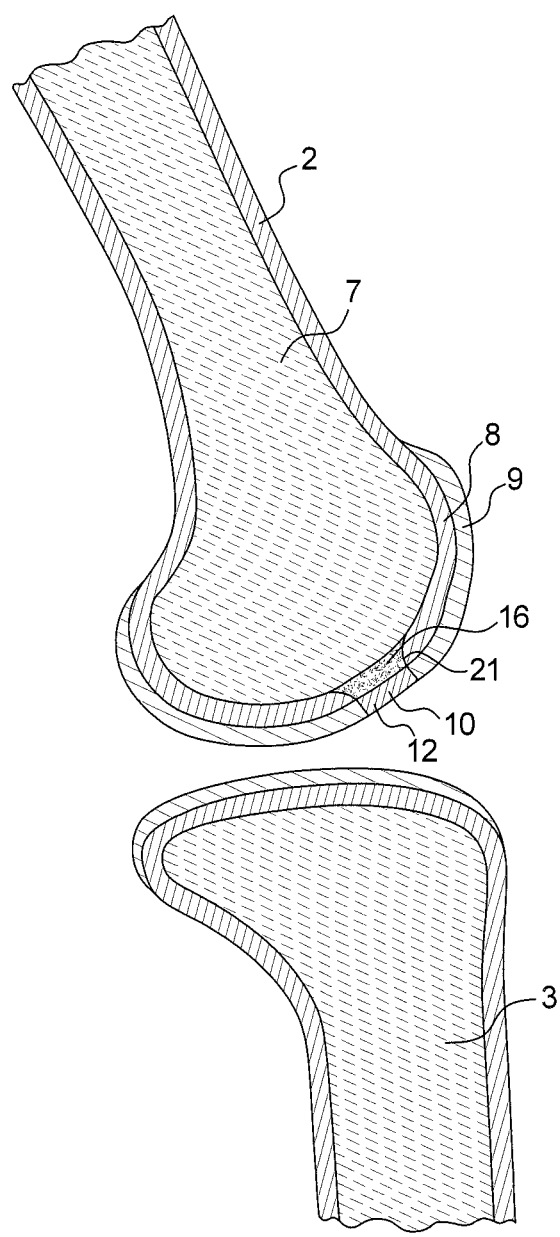
FIG. 5 is a cross-sectional view of a knee joint shown with the orthopedic implant of FIG. 3 implanted therein.

Additionally, as shown in FIGS. 3 and 4, the outer periphery or boundary of bone contacting layer 16 may be larger than the outer periphery of articulating layer 12 or vice versa. In particular, implant 10 may be formed such that one of articulating layer 12 and bone contacting layer 16 has a greater length or width than the other of articulating layer 12 and bone contacting layer 16. For example, as shown in FIGS. 3 and 4, bone contacting layer 16 may have a greater width at bone contacting surface 18 than the maximum width of articulating layer 12. In this embodiment, sidewall 21 is tapered such that bone contacting layer 16 increases in width in the direction of bone contacting layer 16. In other embodiments wherein sidewall 21 does not include a taper and is straight between the bottom surface 18 and the top surface 19, this difference in outer periphery may be accomplished by a stepped construct wherein the bone contacting layer 16 has a uniform width or length that is larger than that of the width or length of the articulating layer 12. As a result, the portion of bone contacting layer 16 adjacent to bone contacting surface 18 may be positioned beneath healthy articular cartilage adjacent to the implant site, as shown in FIG. 5. This facilitates the retention and stabilization of implant 10 in position once implanted. Specifically, implant 10 may be implanted such tapered sidewall 21 of bone contacting layer 16 is located beneath adjacent compact bone 8 and/or cartilage layer 9. The compact bone 8 and cartilage layer 9 engage tapered sidewall 21 to assist in preventing implant pull out. In one embodiment, implant 10 may be implanted in a manner that places tapered sidewall 21 under compact bone 8 and/or articulating cartilage layer 9. In another embodiment, bone 8 and cartilage layer 9 may regenerate and heal around tapered sidewall 21 of implant 10. As compared to bone plugs 6 of FIG. 2, implant 10 is much thinner and can be implanted at a depth that is less than that which is required for the implantation of bone plugs 6.

Figure 6:
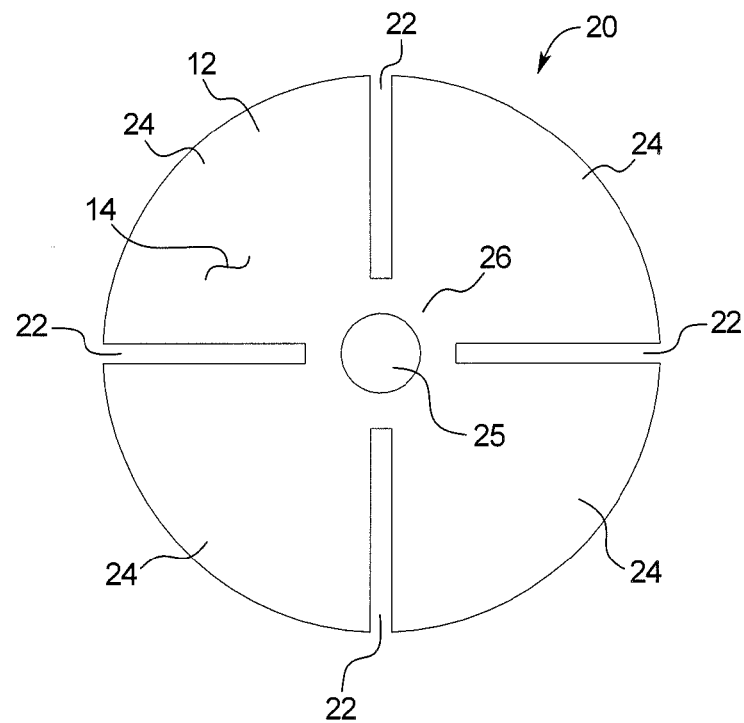
FIG. 6 is a plan view of another exemplary embodiment of the orthopedic implant of the present invention.
Figure 7:
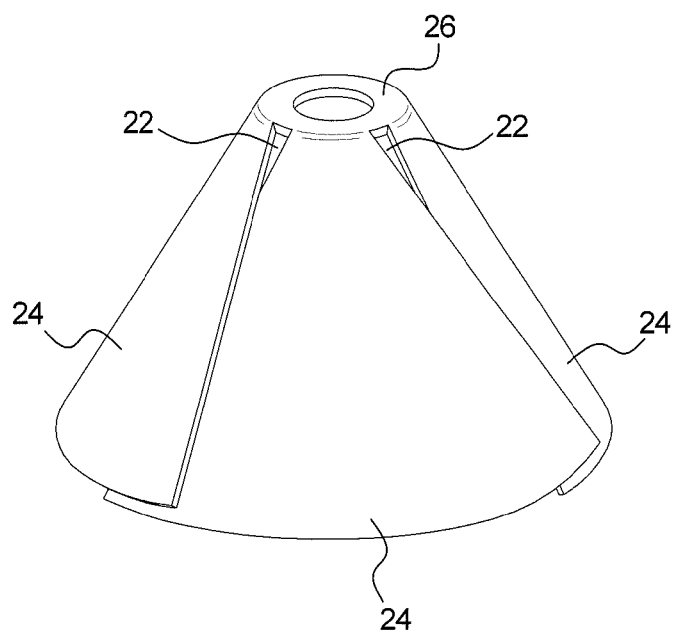
FIG. 7 is a perspective view of the orthopedic implant of FIG. 6 shown in a folded condition or configuration.
Figure 8:
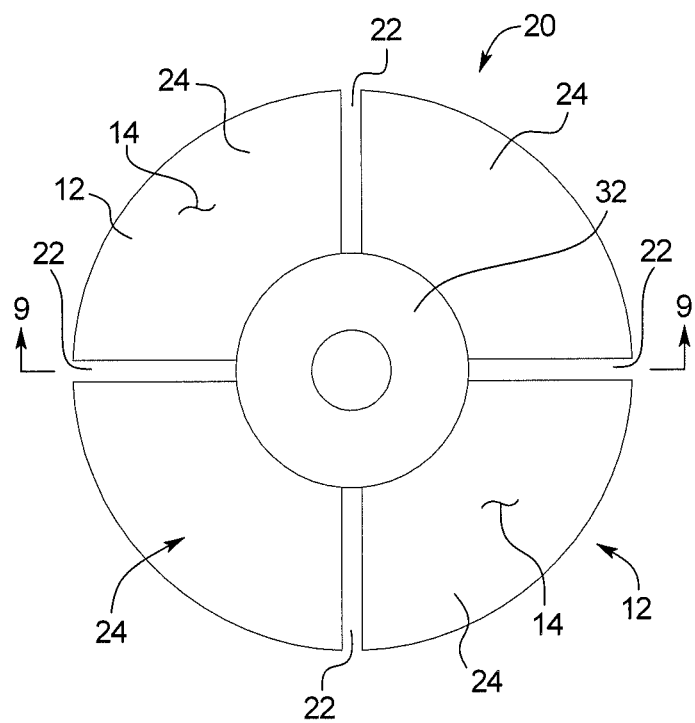
FIG. 8 is a plan view of the orthopedic implant of FIG. 6 including a bone anchor.
Figure 9:
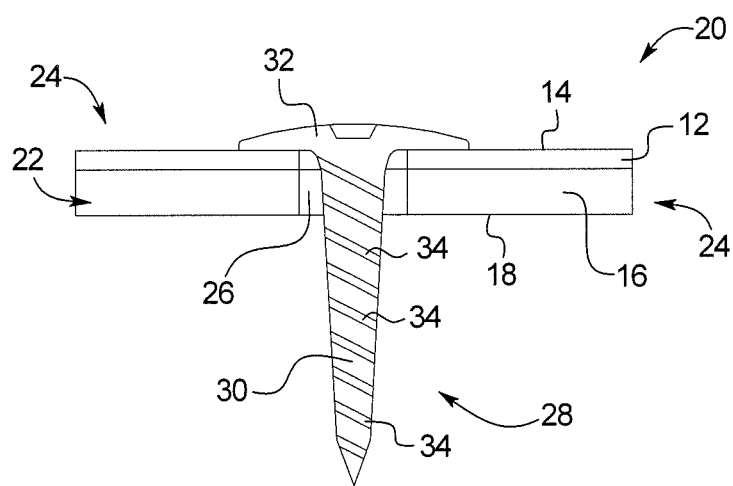
FIG. 9 is a cross-sectional view of the orthopedic implant and bone anchor of FIG. 8 taken along line 9-9 of FIG. 8.

Referring to FIGS. 6-9, another exemplary embodiment of an orthopedic implant made according to the present invention is shown as orthopedic implant 20. Implant 20 may be formed in a substantially similar manner as implant 10, described in detail above, and like reference numerals will be used to identify corresponding parts therebetween. Similar to implant 10, implant 20 includes a bone contacting layer 16 and an articulating layer 12, as shown in FIG. 9. Referring to FIGS. 6 and 8, implant 20 includes slots 22 which define a plurality of adjacent sections 24. As shown, slots 22 extend radially from the exterior periphery of implant 20 toward the middle of implant 20. However, slots 22 terminate prior to reaching the center of implant 20, resulting in the formation of central portion 26 (FIG. 6) of implant 20. Each section 24 of implant 20 terminates at central portion 26, resulting in central portion 26 functioning to connect each section 24 to one another. In the illustrated embodiment, slots 22 are completely devoid of any material. In other embodiments, however, slots 22 may be formed from a reduced material thickness and/or reduced bending stiffness or may be formed from a different material from that of sections 24. Advantageously, the use of slots 22 and sections 24 allows for implant 20 to be collapsible, e.g., to be folded upon itself, during implantation of implant 20, as illustrated in FIG. 7. As a result, implant 20 may be passed through a substantially smaller incision.

Figure 10:
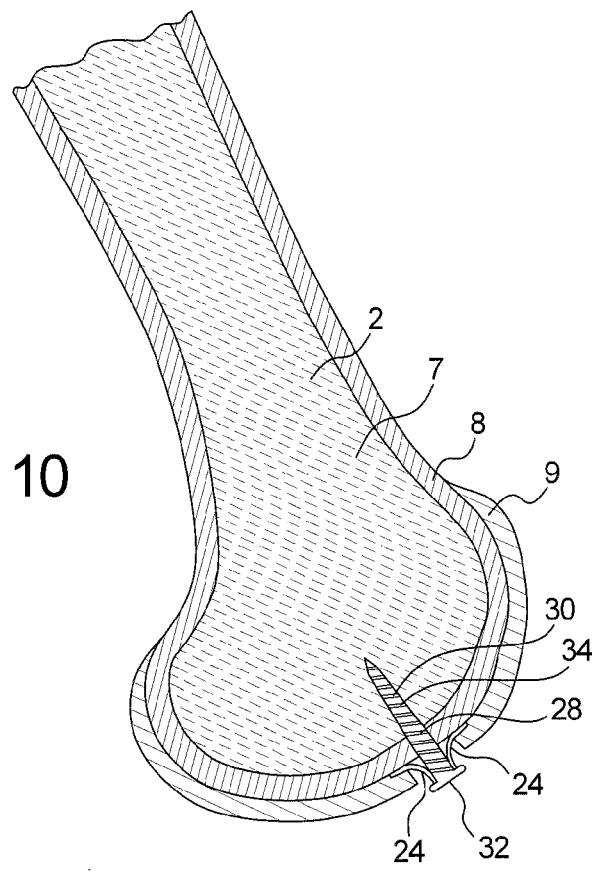
FIG. 10 is a cross-sectional view of a femur shown with the orthopedic implant of FIG. 6 implanted therein.
Figure 11:
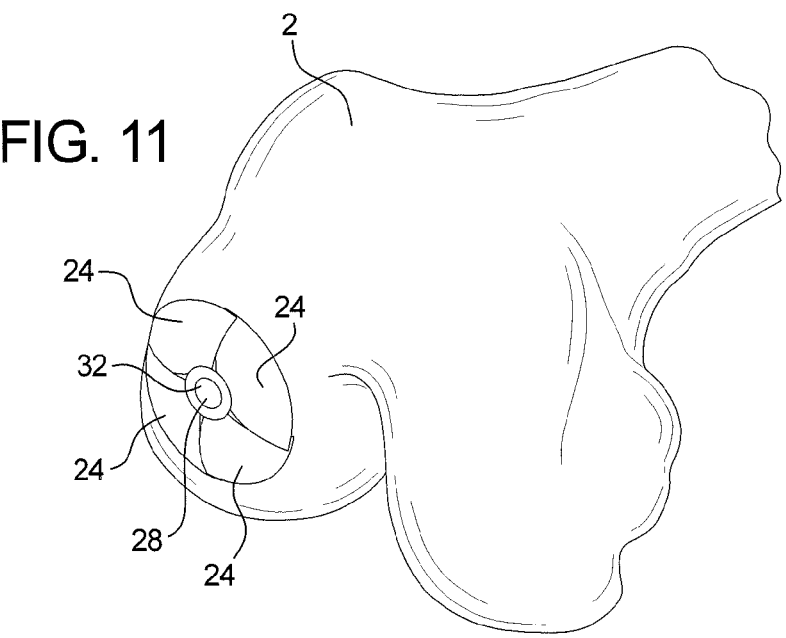
FIG. 11 is a perspective view of a femur having the orthopedic implant of FIG. 6 implanted therein.

As shown in FIGS. 8 and 9, implant 20 may be used in conjunction with an anchor 28. As illustrated in FIGS. 10 and 11, anchor 28 assists in securing implant 20 to an individual's bone. Referring to FIGS. 9 and 10, anchor 28 includes shaft 30 and head 32. In one exemplary embodiment, shaft 30 includes threads 34 to provide threaded fixation of bone anchor 28 to an individual's bone. In other exemplary embodiments, anchor 28 may lack threads 34 and may frictionally engage an individual's bone to secure implant 20 thereto. In one exemplary embodiment, implant 20 may include an opening 25 (FIG. 6) for the receipt of shaft 30 of anchor 28 therein. Alternatively, implant 20 may be formed such that anchor 28 may pass through implant 20 during implantation. As a result, anchor 28 may be secured in any location through implant 20. This allows the surgeon to identify the preferred area for the insertion of anchor 28, such as the area with the greatest bone stock.

Additionally, as shown in FIGS. 8 and 9, head 32 of anchor 28 is sized to extend over a portion of slots 22 in an exemplary embodiment. By extending over a portion of slots 22, head 32 of anchor 28 functions to secure sections 24 of implant 20 to the bone and prevent sections 24 from folding over onto themselves or onto adjacent sections 24 or otherwise experiencing significant movement once implanted that could impact the function of implant 20.

Anchor 28 may be formed form any biocompatible material, including metals and polymers. In one exemplary embodiment, anchor 28 is formed from a bioresorbable material, such as a bioresorbable polymer. Advantageously, when anchor 28 is formed from a bioresorbable material, anchor 28 will be adsorbed by the individual's body as bone contacting layer 16 of implant 20 begins to provide osseointegration with the individual's bone. This eliminates both the need for a permanent bone anchor that must remain within the individual's bone and also eliminates the need to remove the bone anchor once osseointegration is established.

To implant one of implants 10, 20, the implantation site may by prepared by roughening the individual's bone to cause bleeding that facilitates bone ingrowth. In one embodiment, a minimal amount of bone is resected, i.e., substantially less bone is resected during the present procedure than is resected during a mosaicplasty procedure. For example, if an implant having a shape substantially similar to the shape of implant 10 as shown in FIGS. 3 and 4 is used, a small portion of the bone may be chiseled out. In one exemplary embodiment, a mortiser chisel type instrument is used to prepare the site. Such an instrument may also be used when implant 10 is formed as a specific geometric shape, such as a rectangle. Alternatively, in other embodiments where the implant of the present invention is round, a flat bottom end mill may be used to prepare the site by removing a minimal amount of bone. For example, a flat bottom end mill may be used to prepare the implantation site for implant 20 when implant has the shape shown in FIGS. 8 and 9. Once the site is prepared, any known inserter or positioning device may be used to position and seat the implants of the present invention at the implantation site. Furthermore, when implant 20 is being implanted into femur 2, sections 24 may be bent into the configuration shown in FIG. 7. As implant 20 is being inserted into femur 2, the periphery of sections 24 may be positioned beneath articular cartilage layer 9 adjacent to the implant site.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopedic device for repairing an articular cartilage defect, comprising:
    an implant including a plurality of sections each separated by slots wherein the sections fold relative to each other, one or more of the slots extending radially from a periphery of the implant toward a center of the implant and terminating prior to the center so as to define a central portion including an orifice configured to at least partially receive a bone anchor, the implant including:
    a bone contacting layer formed from a first material, the bone contacting layer including a top surface and a bottom bone contacting surface, the bone contacting layer having a thickness of less than about 3 millimeters between the top surface and bottom bone contacting surface; and
    an articulating layer at least partially superimposed over the bone contacting layer, the articulating layer formed from a second material that is different from the first material, the articulating layer including a top articulating surface and a bottom surface, the articulating layer having a thickness of less than about 2 millimeters between the top and bottom surfaces of the articulating layer.

2. The orthopedic device of claim 1 in which the implant is generally reniform shaped.

3. The orthopedic device of claim 1 in which the implant is generally arcuate.

4. The orthopedic device of claim 1 in which the slots are adapted to allow the implant to be folded into a desired configuration.

5. The orthopedic device of claim 1 in which the bone contacting layer has an outer periphery and the articulating layer has an outer periphery, and the outer periphery of the bone contacting layer is larger than the outer periphery of the articulating layer.

6. The orthopedic device of claim 1 in which the bone contacting layer includes one or more tapered sidewalls extending between the to surface and the bottom bone contacting surface.

7. The orthopedic device of claim 1 wherein the implant has an overall thickness of less than 5 millimeters as measured between the bottom bone contacting surface of the bone contacting layer and the top articulating surface of the articulating layer.

8. The orthopedic device of claim 1 wherein said first material is a porous material.

9. The orthopedic device of claim 1, wherein said second material is a polymer.

10. An orthopedic device for repairing an articular cartilage defect, comprising:
    an implant including an articulating layer at least partially superimposed over a bone contacting layer, the implant further including a plurality of sections separated by slots wherein the sections are configured to fold relative to each other so as to permit the implant to be collapsible, one or more of the slots extending radially from a periphery of the implant to define a central portion including an orifice configured to at least partially receive a bone anchor;
    the bone contacting layer formed from a first material and having an outer periphery, the bone contacting layer including a top surface, a bottom bone contacting surface and one or more sidewalls extending therebetween, the bone contacting layer having a thickness of less than about 3 millimeters between the top surface and the bottom bone contacting surface; and
    the articulating layer formed from a second material that is different from the first material, the articulating layer including a top articulating surface and a bottom surface, the articulating layer having a thickness of less than about 2 millimeters between the top articulating surface and the bottom surface of the articulating layer, and the articulating layer having an outer periphery that is smaller than the outer periphery of the bone contacting layer.

11. The orthopedic device of claim 10 in which the implant is generally reniform shaped.

12. The orthopedic device of claim 10 in which one or more of the sidewalls of the bone contacting layer are tapered.

13. The orthopedic device of claim 10 wherein the implant has an overall thickness of less than about 5 millimeters as measured between the bone contacting surface of the bone contacting layer and the top articulating surface of the articulating layer.

14. The orthopedic device of claim 10, wherein said first material is a porous material.

15. The orthopedic device of claim 10, wherein said second material is a polymer.

16. An orthopedic device for repairing an articular cartilage defect, comprising:
    an implant including an articulating layer at least partially superimposed over a bone contacting layer, the implant further including a plurality of sections separated by slots wherein the sections fold relative to each other, one or more of the slots extending radially from a periphery of the implant to define a central portion including an orifice configured to at least partially receive a bone anchor;
    the bone contacting layer formed from a first material and including a top surface and a bottom bone contacting surface, the bone contacting layer having a thickness of less than about 3 millimeters between the top surface and bottom bone contacting surface; and the articulating layer formed from a second material that is different from the first material, the articulating layer including a top articulating surface and a bottom surface, the articulating layer having a thickness of less than about 2 millimeters between the top articulating surface and the bottom surface of the articulating layer.

17. The orthopedic device of claim 16 in which the implant is generally arcuate.

18. The orthopedic device of claim 16 wherein said first material is a porous material.

19. The orthopedic device of claim 16 wherein said second material is a polymer.

20. The orthopedic device of claim 16 further including a bone anchor for attaching the implant to a bone.

* * * * *

UNITED STATES PATENT AND TRADEMARK OFFICE
CERTIFICATE OF CORRECTION

| | | |
|---|---|---|
| PATENT NO. | : 8,668,739 B2 | Page 1 of 1 |
| APPLICATION NO. | : 13/204083 | |
| DATED | : March 11, 2014 | |
| INVENTOR(S) | : Blanchard et al. | |

It is certified that error appears in the above-identified patent and that said Letters Patent is hereby corrected as shown below:

In the Claims

In column 10, line 3, in claim 6, delete "to" and insert --top--, therefor

Signed and Sealed this
Second Day of December, 2014

Michelle K. Lee
*Deputy Director of the United States Patent and Trademark Office*